United States Patent [19]

Junino et al.

[11] Patent Number: 4,865,617
[45] Date of Patent: Sep. 12, 1989

[54] DYEING COMPOSITIONS FOR KERATINOUS FIBRES, ESPECIALLY FOR HUMAN HAIR, CONTAINING OXIDATION DYE PRECURSORS AND HETEROCYCLIC COUPLERS

[75] Inventors: Alex Junino, Livry-Gargan; Alain Genet, Aulnay-sous-Bois; Gerard Lang, Saint-Gratien, all of France

[73] Assignee: L'Oreal, Paris, France

[21] Appl. No.: 92,720

[22] Filed: Sep. 3, 1987

[30] Foreign Application Priority Data

Sep. 4, 1986 [LU] Luxembourg .............................. 86.571

[51] Int. Cl.⁴ ...................... A61K 7/13; C07D 317/44
[52] U.S. Cl. ......................................... 8/409; 549/437; 8/406; 8/407; 8/408; 8/423
[58] Field of Search .................... 8/409, 406, 407, 408, 8/423; 549/437

[56] References Cited

U.S. PATENT DOCUMENTS 4,395,262 7/1983 Konrad et al. .......................... 8/409

FOREIGN PATENT DOCUMENTS

EP0004366 10/1979 European Pat. Off. ................ 8/409

*Primary Examiner*—Paul Lieberman
*Assistant Examiner*—Christine A. Skane
*Attorney, Agent, or Firm*—Marshall, O'Toole, Gerstein, Murray & Bicknell

[57] ABSTRACT

The invention relates to a dyeing composition for keratinous fibres containing, in a cosmetically acceptable solvent medium, at least one para-type oxidation dye precursor in combination with at least one heterocyclic coupler of formula:

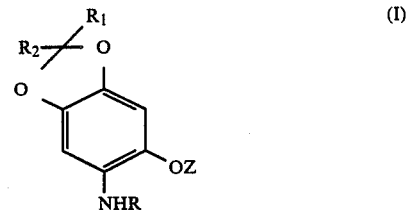

in which R denotes a hydrogen atom, a $C_1$-$C_4$ radical, a $C_2$-$C_4$ hydroxyalkyl radical, a $C_3$ to $C_6$ polyhydroxyalkyl radical, or a $C_2$-$C_6$ alkoxyalkyl radical, Z, independently of R, denotes a $C_1$ to $C_4$ alkyl radical, a $C_2$ to $C_4$ hydroxyalkyl radical, a $C_3$ to $C_6$ polyhydroxyalkyl radical, a $C_2$-$C_6$ alkoxyalkyl radical or a trifluoroethyl radical, $R_1$ and $R_2$ independently of each other denote a hydrogen atom or a $C_1$ to $C_4$ alkyl radical, or one of the addition salts of the compound of formula (I) with an inorganic acid, a process for the oxidation dyeing of hair using this composition as well as the new couplers of formula (I) where Z is other than methyl when $R_1$, $R_2$ and R=H, the process for their preparation, the new intermediate compounds of formula:

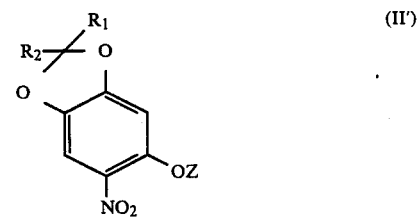

and the process for their preparation.

23 Claims, No Drawings

DYEING COMPOSITIONS FOR KERATINOUS FIBRES, ESPECIALLY FOR HUMAN HAIR, CONTAINING OXIDATION DYE PRECURSORS AND HETEROCYCLIC COUPLERS

The present invention relates to new dyeing compositions for keratinous fibres and especially for human hair, containing oxidation dye precursors, a dyeing process employing the said compositions, new heterocyclic couplers and the process for their preparation, as well as the new intermediate compounds employed in this process and the process for their preparation.

It is known that the use of dyeing compositions containing oxidation dye precursors and especially p-phenylenediamines and ortho- or para-aminophenols, which are generally referred to by the term of oxidation bases, is known for dyeing keratinous fibres and especially human hair.

It is also known that colour modifiers or couplers, and especially aromatic meta-diamines, meta-aminophenols and meta-diphenols are employed in order to modify the shades obtained with these oxidation bases.

The hair dye formulator requires oxidation dye precursors or couplers which make it possible to impart to hair, in an oxidizing alkaline medium employed in oxidation dyeing, colours which have satisfactory resistance to light, to washing, to inclement weather and to perspiration.

However, in addition to the abovementioned essential qualitites, the formulator increasingly needs oxidation dye precursors and/or couplers which make it possible to obtain low-selectivity dyes, that is to say colours which are substantially identical on natural hair and on hair sensitized by a treatment such as bleaching or permanent waving. It has been found, in fact, that hair whose roots are natural and whose ends have already been subjected to various treatments such as bleaching or permanent waving varies in its degree of sensitivity to the dye, which is reflected in poor colour uniformity between the root and the end of the hair, which is particularly unattractive.

The Applicant has found that all the above requirements could be satisfied by virtue of the use of a dyeing composition containing, in a cosmetically acceptable solvent, medium, a tinctorially effective amount of at least one oxidation dye precursor of the "para" type in combination with at least one heterocyclic coupler corresponding to the following formula (I):

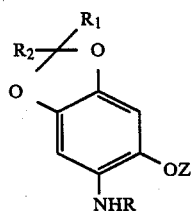

in which R denotes a hydrogen atom, a $C_1$–$C_4$ alkyl radical, a $C_2$–$C_4$ hydroxyalkyl radical, a $C_3$ to $C_6$ polyhydroxyalkyl radical or a $C_2$–$C_6$ alkoxyalkyl radical, independently of R, Z denotes a $C_1$–$C_6$ alkyl radical, a $C_2$–$C_4$ hydroxyalkyl radical, a $C_3$–$C_6$ polyhydroxyalkyl radical, a trifluoroethyl radical or a $C_2$–$C_6$ alkoxyalkyl radical, and $R_1$ and $R_2$, which are identical or different, denote a hydrogen atom or a $C_1$–$C_4$ alkyl radical, or an addition salt thereof with an inorganic acid such as hydrochloric acid, hydrobromic acid or sulphuric acid.

According to a preferred embodiment, R and Z do not simultaneously denote a polyhydroxyalkyl radical.

When applied to keratinous fibres and especially to human hair, the dyeing composition defined above makes it possible to obtain, under the usual conditions of oxidation dyeing, shades which are stable to light, to washing and to inclement weather, and which have low selectivity, that is to say which are substantially identical on natural hair and on hair sensitized by a treatment such as bleaching or permanent waving.

Furthermore, the combination of a coupler of formula (I) with an oxidation dye precursor of the "para" type such as a p-phenylenediamine or certain p-aminophenols, like 3-methoxy-4-aminophenol, makes it possible to obtain pure green shades which are particularly sought after by the person skilled in the art for producing matt shades, for toning down shades which are too vivid or too red and for applying a correction, where appropriate, to the tendency to reddening with time possessed by certain dyes.

Another subject of the present invention is a process for dyeing keratinous fibres and especially human hair, employing the dyeing compositions defined above and making use of development with an oxidizing agent.

Another subject of the present invention is the new heterocyclic couplers of formula (I'):

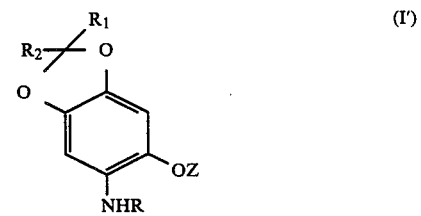

in which R denotes a hydrogen atom, a $C_1$–$C_4$ alkyl radical, a $C_2$–$C_4$ hydroxyalkyl radical, a $C_3$ to $C_6$ polyhydroxyalkyl radical or a $C_2$–$C_6$ alkoxyalkyl radical, Z denotes a $C_1$–$C_4$ alkyl radical, a $C_2$–$C_4$ hydroxyalkyl radical, a $C_3$–$C_6$ polyhydroxyalkyl radical, a trifluoroethyl radical or a $C_2$–$C_6$ alkyoxalkyl radical, $R_1$ and $R_2$ independently of each other denote a hydrogen atom or a $C_1$–$C_4$ alkyl radical;

provided that when R, $R_1$ and $R_2$ denote a hydrogen atom, Z is other than a methyl radical, as well as the addition salts formed by these compounds with an inorganic acid.

The preferred compounds (I') are those in which R and Z do not simultaneously denote a polyhydroxyalkyl radical.

The present invention also relates to the process for the preparation of the new heterocyclic couplers of formula (I').

The compound of formula (I') is prepared in one or more stages from the compound of formula (II) according to the following reaction scheme:

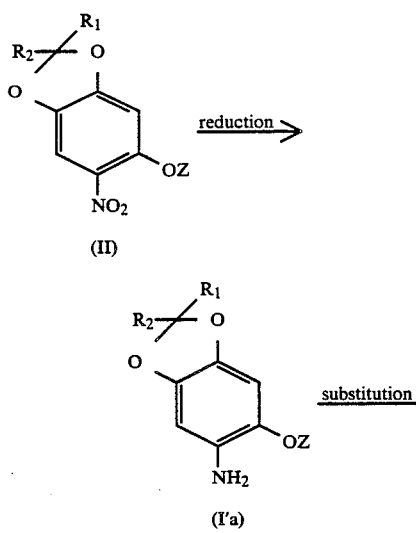

(II)

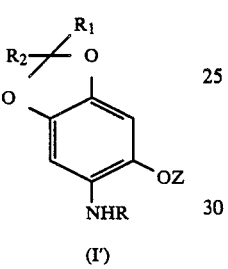

(I'a)

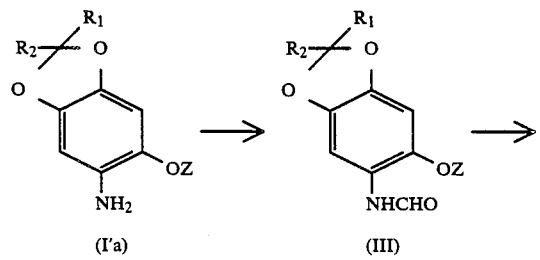

(I')

R, Z, R₁ and R₂ having the meanings indicated earlier.

The compound of formula (I'a) is obtained either by catalytic reduction of the compound of formula (II) under hydrogen pressure, in the presence of solvent and of a catalyst such as palladium on charcoal (a reduction described for the preparation of 4-amino-5-methoxy-1,2-methylenedioxybenzene in Z. Naturforsch. 33c, p.459–464 (1978) and in Monatsch. Chem. 88, p.541-559 (1957)), or by reduction of the compound of formula (II) using iron in the presence of acetic acid.

The compound of formula (I') in which R is not a hydrogen atom is obtained from the compounds (I'a) by conventional methods for the alkylation, hydroxyalkylation or alkoxyalkylation of aromatic amines.

Among these methods, the Applicant has found that the most advantageous alkylation method, bearing in mind the presence of the methylenedioxy group in the molecule, consists, in a first step, in N-formylating the compound (I'a) to obtain the compound (III). In a second step the compound (III) is alkylated in a basic medium to give the compound (IV which, when subjected to the action of an inorganic acid, makes it possible to obtain the compound (I') in which R is an alkyl radical, in accordance with the following reaction scheme:

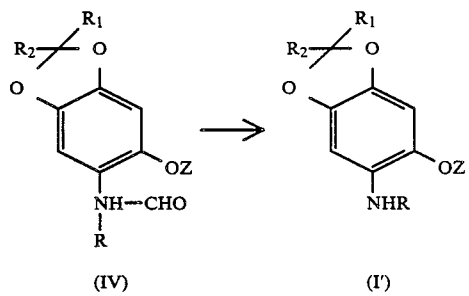

(I'a) (III)

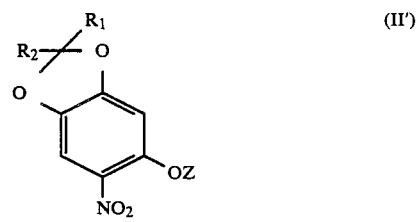

(IV) (I')

R, Z, R₁ and R₂ having the meanings indicated earlier, with R not denoting a hydrogen atom.

Among the preferred hydroxyalkylation methods, there may be mentioned the action of β-chloroethyl chloroformate on the compound (I'a), which, in a first step, makes it possible to obtain the corresponding β-chloroethyl carbamate which, in a second step, subjected to the action of a strong inorganic base such as sodium hydroxide or potassium hydroxide, makes it possible to obtain the compound (I') in which the radical R is a β-hydroxyethyl radical.

Another subject of the present invention is the new intermediate compound of the following formula (IIβ):

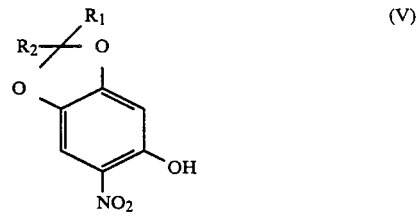

(II')

in which Z denotes a $C_2$–$C_4$ alkyl radical, a $C_2$–$C_4$ hydroxyalkyl radical, a $C_3$–$C_6$ polyhydroxyalkyl radical, a trifluoroethyl radical or a $C_2$–$C_6$ alkoxyalkyl radical, and $R_1$ and $R_2$ independently of each other denote a hydrogen atom or a $C_1$–$C_4$ alkyl radical.

Another subject of the present invention is the process for the preparation of the compound of formula (II').

The compound of formula (II') in which the radical Z is not the trifluoroethyl radical may be prepared:

a) either by the reaction of a dialkyl sulphate, or an alkyl, hydroxyalkyl, polyhydroxyalkyl or alkoxyalkyl halide with the compound of formula:

(V)

$R_1$ and $R_2$ having the meanings referred to above, in the presence of an alkaline agent such as a carbonate and of a solvent which may be benzene or dimethylformamide; the compound of formula (IV) for which $R_1=R_2=H$ is described in J. Org. Chem. vol. 24, p.

327–329 (1959) and in J.A.C.S., vol. 64, p. 2983–2986 (1942);

the compounds of formula (V) for which $R_1$ and $R_2$ denote an alkyl radical may be obtained from the 2,2-disubstituted 1,3-benzodioxole which is acetylated by lead tetraacetate and nitrated according to conventional methods using dilute nitric acid in the presence or absence of acetic acid and then hydrolysed according to the following reaction scheme

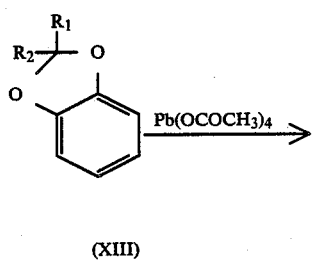

(XIII)

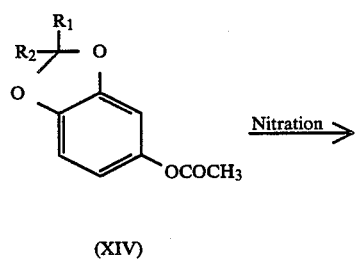

(XIV)

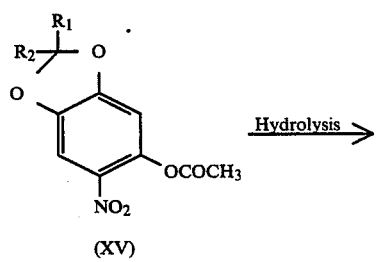

(XV)

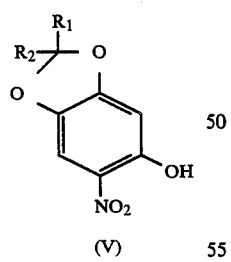

(V)

compounds of formula (XIII) may be obtained by the reaction of a ketone $R_1COR_2$ on the pyrocatechol as indicated in AUST.J.CHEM (1980) Vol 33 (3) p.675–80;

compounds of formula (XIV) may be obtained according to the method described in AUST.J.CHEM (1980) Vol.33 (3) p.527–43;

b) or by nitrating using dilute nitric acid in the presence or absence of acetic acid, at a temperature of between 5° C. and 30° C., the compound of formula:

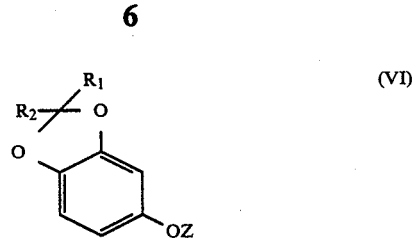

where Z, $R_1$ and $R_2$ have the meanings indicated earlier with the exception of trifluoroethyl in the case of Z; this route is preferably employed in the case of the compounds of formula (II') where Z denotes an alkyl or alkoxyalkyl radical.

The compound of formula (VI) is prepared:
a) either from the compound (VII) of formula:

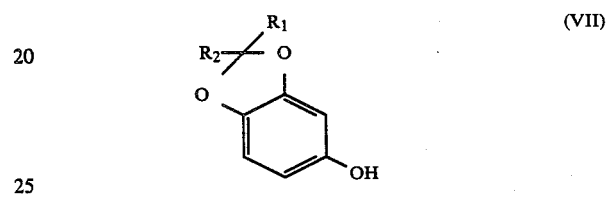

where $R_1$ and $R_2$ have the abovementioned meanings, by the action of an alkyl, hydroxyalkyl, polyhydroxyalkyl or alkoxyalkyl halide or of a dialkyl sulphate, according to the conventional procedures for alkylation, hydroxyalkylation or alkoxyalkylation of phenols;

the compounds of formula (VII) in which $R_1$ and $R_2$ denote an alkyl radical may be obtained in hydrolysing the compounds of formula (XIV).

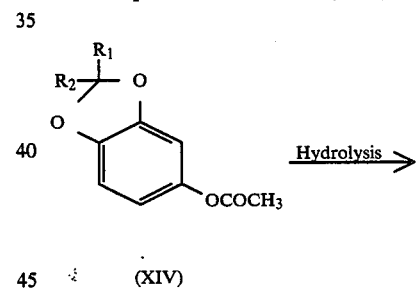

(XIV)

(VII)

b) or from the compound (VIII) of formula:

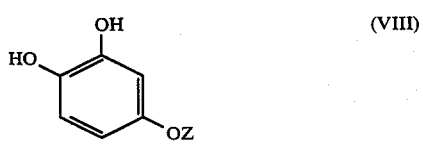

where Z has the meanings indicated earlier, except for trifluoroethyl, by the action of a dihalomethane, an aldehyde or a ketone of formula:

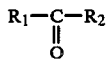

according to conventional procedures, especially those described in "Protective groups in organic synthesis", T.W. Greene, John Wiley, Interscience, 1981, p. 108-112.

4-Methoxy-5-nitro-1,2-methylenedioxybenzene, a known compound of formula (II), is prepared either from 4-hydroxy-5-nitro-1,2,-methylenedioxybenzene according to Monatsch. Chem. 88, p. 541-559 (1957) by reaction with dimethyl sulphate in the presence of sodium carbonate and of toluene, or from 4-methoxy-1,2-methylenedioxybenzene according to J. Agric.Food Chem. vol.15, p.140 (1967) or according to Z.Naturforsch. 33c, p. 459-464 (1978) by nitration with nitric acid in the presence of acetic acid.

The compound of formula (II') in which Z is the trifluoroethyl radical is prepared from 4,5-dinitro-1,2-methylenedioxybenzene.

The Applicant has shown that the reaction of an alcohol Z—OH, in the presence of a strong base such as potassium hydroxide, with 4,5-dinitro-1,2-methylenedioxybenzene of formula (IX), the excess alcohol Z—OH being used as solvent, yielded the dinitrophenol of formula (X) when the radical Z is an alkyl, hydroxyalkyl or polyhydroxyalkyl radical:

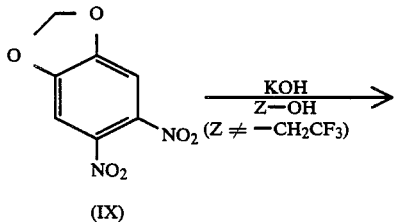

Under the same conditions, and in a totally surprising manner, when the alcohol Z—OH is trifluoroethanol, the compound of formula (II') in which Z denotes a trifluoroethyl radical is obtained selectively in a good yield, in accordance with the following reaction scheme:

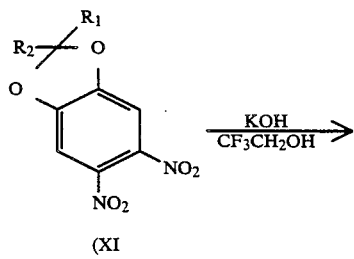

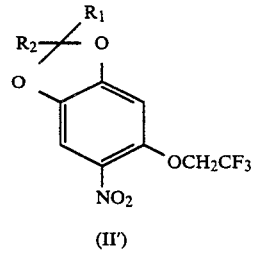

As preferred radicals R which appear in the formulae (I) and (I'), there may be mentioned hydrogen, and methyl, ethyl, n-propyl, n-butyl, β-hydroxyethyl, β-hydroxypropyl, γ-hydroxypropyl and β,γ-dihydroxypropyl radicals.

As preferred radicals Z in the formulae (I), (I'), (I'a), (II) and (II'), there may be mentioned trifluoroethyl, methyl, ethyl, n-propyl, n-butyl, β-hydroxyethyl, β-hydroxypropyl, γ-hydroxypropyl and β,γ-dihydroxypropyl radicals.

Among the preferred compounds of formula (I') there may be mentioned:
4-(β-hydroxyethyl)amino-5-methoxy-1,2-methylenedioxybenzene
4-amino-5-(2',2',2'-trifluoroethoxy)-1,2-methylenedioxybenzene
4-methylamino-5-methoxy-1,2-methylenedioxybenzene
4-amino-5-(β-hydroxyethoxy)-1,2-methylenedioxybenzene and
6-amino-5-methoxy-2-methyl-2-propyl-1,3-benzodioxole, as well as their addition salts with an inorganic acid.

By way of compounds of formula (II') there may be mentioned 4-nitro-5-(β-hydroxyethoxy)-1,2-methylenedioxybenzene, 4-nitro-5-(2',2',2'-trifluoroethoxy)-1,2-methylenedioxybenzene and 5-methoxy-6-nitro-2-methyl-2-propyl-1,3-benzodioxole.

The para-type oxidation dye precursors employed in combination with the heterocyclic couplers of formula (I) in the dyeing compositions for keratinous fibres according to the invention are chosen from p-phenylenediamines, p-aminophenols, and heterocyclic para precursors such as 2,5-diaminopyridine, 2-hydroxy-5-aminopyridine or tetraaminopyrimidine.

By way of p-phenylenediamines there may be mentioned the compounds corresponding to the formula (XII) below:

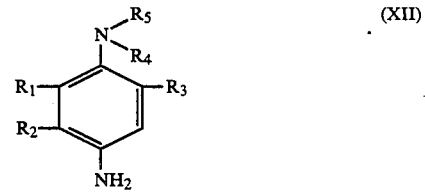

in which $R_1$, $R_2$ and $R_3$ are identical or different and denote a hydrogen or halogen atom, an alkyl radical containing 1 to 4 carbon atoms, an alkoxy radical containing 1 to 4 carbon atoms, $R_4$ and $R_5$ are identical or different and denote a hydrogen atom or an alkyl, hydroxyalkyl, alkoxyalkyl, carbamylkalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ containing from 1 to 4 carbon atoms, or else $R_4$ and $R_5$, together with the nitrogen atom to which they are linked, can form a piperidino or morpholino heterocyclic ring provided that $R_1$ or $R_3$ or both $R_1$ and $R_3$ denote a hydrogen atom when $R_4$ and $R_5$ do not denote a hydrogen atom, and the cosmetically acceptable salts of these compounds.

Among the compounds of formula (XII) there may be mentioned p-phenylenediamine, p-tolylenediamine, methoxy-para-phenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di($\beta$-hydroxyethyl)-para-phenylenediamine, 3-methyl-4-amino-N,N-di($\beta$-hydroxyethyl)aniline, 3-chloro-4-amino-N,N-di($\beta$-hydroxyethyl)aniline, 4-amino-N,N-(ethyl, carbamylmethyl)aniline, 3-methyl-4-amino-N,N-(ethyl, carbamylmethyl)-aniline, 4-amino-N,N-(ethyl, $\beta$-piperidinoethyl)aniline, 3-methyl-4-amino-N,N-(ethyl, $\beta$-piperidinoethyl)aniline, 4-amino-N,N-(ethyl, $\beta$-morpholionethyl)aniline, 3-methyl-4-amino-N,N-(ethyl, $\beta$-morpholionethyl)aniline, 4-amino-N,N-(ethyl, $\beta$-acetylaminoethyl)aniline, 4-amino-N,$\beta$-methoxyethylaniline, 3-methyl-4-amino-N,N-(ethyl, $\beta$-acetylaminoethyl)aniline, 4-amino-N,N-(ethyl, $\beta$-mesylaminoethyl)aniline, 3-methyl-4-amino-N,N-(ethyl, $\beta$-mesylaminoethyl)aniline, 4-amino-N,N-(ethyl, $\beta$-sulphoethyl)aniline, 3-methyl-4-amino-N,N-(ethyl, $\beta$-sulphoethyl)aniline, N-[(4'-amino)phenyl]morpholine and N-[(4'-amino)phenyl]piperidine. These para-type oxidation dye precursors may be added to the dyeing composition in the form of free base or in the form of salts, such as in the form of hydrochloride, hydrobromide or sulphate.

Among the p-aminophenols there may be mentioned p-aminophenol, 2-methyl-4-aminophenol, 4-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol and 3-methoxy-4-aminophenol.

The dyeing compositions according to the invention may also contain ortho-type oxidation dye precursors such as ortho-aminophenols, ortho-phenylenediamines, or ortho-diphenols such as 1-amino-2-hydroxybenzene, 6-methyl-1-hydroxy-2-aminobenzene or 4-methyl-1-amino-2-hydroxybenzene.

The dyeing compositions according to the invention containing the heterocyclic coupler of formula (I) may optionally contain other couplers which are known as such, such as meta-diphenols, meta-aminophenols, meta-phenylenediamines, meta-acylaminophenols, meta-ureidophenols, meta-carbalkoxyaminophenols or $\alpha$-naphthol, and the couplers containing an active methylene group such as $\beta$-ketonic compounds and pyrazolones.

By way of example there may be mentioned, in particular, 2,4-dihydroxphenoxyethanol, 2,4-dihydroxyanisole, meta-aminophenol, resorcinol monomethyl ether, 2-methyl-5-aminophenol, 2-methyl-N-($\beta$-hydroxyethyl)-5-aminophenol, 2-methyl-N-($\beta$-mesylaminoethyl)-5-aminophenol, 2,6-dimethyl-3-aminophenol, 6-hydroxybenzomorpholine, 2,4-diaminoanisole, 2,4-diaminophenoxyethanol, 6-aminobenzomorpholine, [2-N-($\beta$-hydroxyethyl)amino-4-amino]phenoxyethanol, 2-amino-4-N-($\beta$-hydroxyethyl)aminoanisole, 2,4-diaminophenyl $\beta,\gamma$-di-hydroxypropyl ether, 2,4-diaminophenoxyethylamine and their salts.

As is well known, direct dyes such as azo or anthraquinone dyes or nitro derivatives of the benzene series may be added to these compositions in order to tinge or to enrich in highlights the colours provided by the oxidation dye precursors.

The total quantity of the para-type oxidation dye precursors and of the couplers employed in the dyeing compositions according to the invention preferably represents from 0.3 to 7% by weight of the said composition. The concentration of compounds (I) may vary between 0.05 and 3.5% of the weight of the total composition.

The cosmetically acceptable medium is generally aqueous and its pH may vary between 8 and 11, and it is preferably between 9 and 11.

It is adjusted to the desired value with an alkalifying agent such as aqueous ammonia, alkali metal carbonates, or alkanolamines such as mono-, di- or triethanolamine.

In the preferred embodiment, the dyeing compositions according to the invention also contain anionic, cationic, nonionic or amphoteric surface-active agents or mixtures thereof. Among these surface-active agents, there may be mentioned more particularly fatty alcohol alkylbenzenesulphonates, alkylnaphthalenesulphonates, sulphates, ether sulphates and sulphonates, quaternary ammonium salts such as trimethylcetylammonium bromide, cetylpyridinium bromide, optionally oxyethylenated fatty acid ethanolamides, polyoxyethylenated acids, alcohols and amines, polyglycerolated alcohols, and polyoxyethylenated or polyglycerolated alkylphenols, as well as polyoxyethylenated alkyl sulphates. The surface-active agents are present in the compositions according to the invention in proportions of between 0.5 and 55% by weight, and preferably between 2 and 50% by weight, based on the total weight of the composition.

These compositions may also contain organic solvents in order to solubilize the compounds that might not be sufficiently soluble in water. Among these solvents, there may be mentioned, by way of example, lower $C_1$–$C_4$ alkanols such as ethanol and isopropanol, glycerol, glycols or glycol ethers such as 2-butoxyethanol, ethylene glycol, propylene glycol, diethylene glycol monoethyl ether and monomethyl ether, and aromatic alcohols such as benzyl alcohol or phenoxyethanol, similar products and mixtures thereof. The solvents are preferably present in a proportion of between 1 and 40% by weight, and in particular between 5 and 30% by weight based on the total weight of the composition.

The thickening agents which may be added to the compositions according to the invention are taken particularly from the group consisting of sodium alginate, gum arabic, cellulose derivatives such as methyl cellulose, hydroxyethyl cellulose, hydroxypropyl cellulose, hydroxymethyl cellulose, carboxymethyl cellulose, acrylic acid polymers and xanthane gum. It is also possible to employ inorganic thickening agents such as bentonite. These thickening agents are preferably present in proportions of between 0.1 and 5% by weight, and in particular between 0.2 and 3% by weight, based on the total weight of the composition.

The compositions may contain antioxidants chosen, in particular, from sodium sulphite, thioglycolic acid, sodium bisulphite, ascorbic acid and hydroquinone. These antioxidants are present in the composition in proportions of between 0.05 and 1.5% by weight, based on the total weight of the composition.

Other adjuvants which may be employed in accordance with the invention are, for example, penetrating agents, sequestering agents, buffers and perfumes.

The dyeing compositions according to the invention may be in various forms such as in the form of liquids, creams, gels or any other suitable form effecting the dyeing of keratinous fibres and especially human hair. They may also be packaged in aerosol bottles in the presence of a propellent agent.

The dyeing compositions according to the invention containing an oxidation dye precursor and a coupler of formula (I) are employed in the methods of dyeing keratinous fibres and especially human hair in accordance with a process making use of development by means of an oxidizing agent.

In accordance with this process, the dyeing composition described above is mixed with an oxidizing solution, in a sufficient quantity, at the time of use and the mixture obtained is then applied to the hair.

The oxidizing solution contains oxidizing agents such as hydrogen peroxide, urea peroxide or persalts such as ammonium persulphate. A 20-volume hydrogen peroxide solution preferably employed.

The mixture obtained is applied to the hair and left in position for 10 to 40 minutes, preferably 15 to 30 minutes, after which the hair is rinsed, washed with a shampoo, rinsed again and dried.

Another method of making use of the coupler of formula (I) according to the invention is to dye the hair using a method involving several steps and consisting, in one of the stages, in applying the para oxidation dye precursor by means of a composition as defined above and, in another stage, in applying the coupler of formula (I). The oxidizing agent is present in the composition which is applied in the second step or else is added onto the keratinous fibres themselves in a third step, the exposure and drying or washing conditions being identical.

The invention will be illustrated better with the aid of the following examples of preparation and application, which do not in any way limit the scope of the invention but which should be considered as being solely illustrative.

PREPARATIVE EXAMPLE NO. 1

Preparation of
4-amino-5-methoxy-1,2-methylenedioxybenzene
hydrochloride

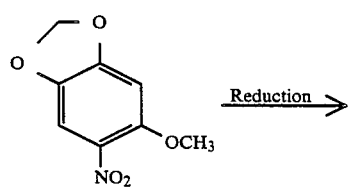

Reduction →

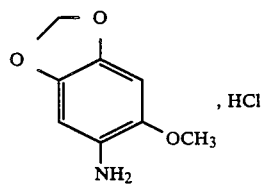

A suspension of 18.5 g of hydrogen-reduced iron powder in 40 ml of ethanol to which 3.3 ml of water and 1.7 ml of acetic acid have been added is heated under reflux. 0.033 mole (6.4 g) of 4-nitro-5-methoxy-1,2-methylenedioxybenzene is added portionwise. The heating is continued for 30 minutes after the end of the addition. 10 ml of absolute ethanol are added and the boiling mixture is then filtered. 20 ml of a 7N solution of hydrochloric acid in absolute ethanol are added to the filtrate. The expected product precipitates. After recrystallization from a water-alcohol mixture, it decomposes at 190°–200° C.

Elemental analysis of the product obtained gives the following results:

| Analysis | Calculated for $C_8H_{10}NO_3Cl$ | Found |
|---|---|---|
| C % | 47.19 | 47.14 |
| H % | 4.95 | 5.00 |
| N % | 6.88 | 6.83 |
| O % | 23.57 | 23.65 |
| Cl % | 17.41 | 17.42 |

PREPARATIVE EXAMPLE NO. 2

Preparation of
4-(β-hydroxyethyl)amino-5-methoxy-1,2-methylenedioxybenzene

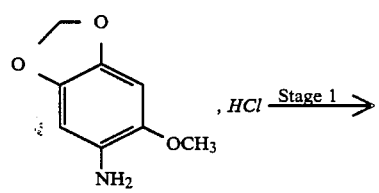

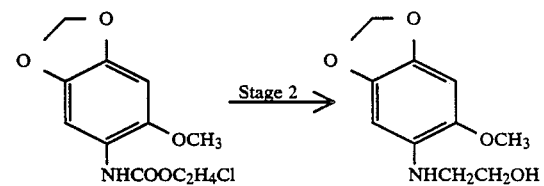

Stage 1: Preparation of β-chloroethyl N-[(2-methoxy-4,5-methylenedioxy)phenyl]carbamate 0.1 mole (20.3 g) of 4-amino-5-methoxy-1,2-methylenedioxybenzene hydroxchloride prepared in Example 1 and 0.12 mole (12 g) of calcium carbonate are heated in 80 ml of dioxane on a boiling water bath. 0.11 mole (15.7 g) of β-chloroethyl chloroformate is added in small portions. After 30 minutes' heating, the reaction mixture is poured onto 300 g of a mixture of ice and water. The reaction mixture is acidified and the expected product is separated by filtering and is reslurried in water.

Stage 2: Preparation of 4-(β-hydroxyethyl)amino-5-methoxy-1,2-methylenedioxybenzene The wet β-chloroethyl N-[(2-methoxy-4,5-methylenedioxy)phenyl]carbamate prepared in the preceding stage is added to 40 ml of water and 40 ml of ethanol containing 0.33 mole of sodium hydroxide pellets. The whole is heated under reflux for 2 hours 30 minutes.

After cooling, the reaction mixture is diluted with 150 ml of iced water and the expected product is separated by filtration; after recrystallization from 96° ethanol it melts at 119° C.

Analysis of the product obtained gives the following results:

| Analysis | Calculated for $C_{10}H_{13}NO_4$ | Found |
|---|---|---|
| C % | 56.86 | 56.77 |
| H % | 6.20 | 6.23 |
| N % | 6.63 | 6.70 |
| O % | 30.30 | 30.12 |

PREPARATIVE EXAMPLE NO. 3

Preparation of 4-amino-5-(2',2',2'-trifluoroethyoxy)-1,2-methylenedioxybenzene

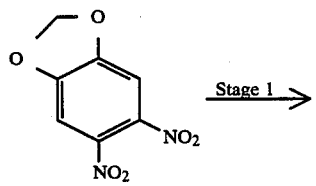

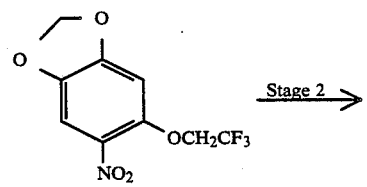

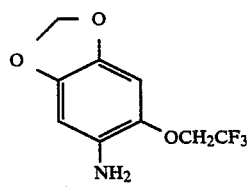

Stage 1: Preparation of 4-nitro-5-(2',2',2'-trifluoroethoxy)-1,2-methylenedioxybenzene 0.4 mole (26.4 g) of 85% strength potassium hydroxide pellets is heated to 70° C. in 0.5 mole (50 g) of 2,2,2-trifluoroethanol and then 10 ml of N-methylpyrrolidone are added. A solution of 0.2 mole (42.4 g) of 4,5-dinitro-1,2-methylenedioxybenzene [(prepared according to Synthesis p 924–925 (1978)] in 42 ml of N-methylpyrrolidone is added dropwise at 60°–65° C. Heating is continued for 30 minutes after the end of the addition. After cooling, the reaction mixture is poured onto 1 liter of iced water. The precipitate of the expected product is filtered off and, after being washed with water and dried under vacuum at 50° C. in the presence of phosphorus pentoxide, is recrystallized from benzene. It melts at 94° C.

Analysis of the product obtained gives the following results:

| Analysis | Calculated for $C_9H_6NO_5F_3$ | Found |
|---|---|---|
| C % | 40.77 | 40.75 |
| H % | 2.28 | 2.28 |
| N % | 5.28 | 5.36 |
| F % | 21.50 | 21.79 |

Stage 2: Preparation of 4-amino-5-(2',2',2'-trifluoroethoxy)-1,2-methylenedioxybenzene A suspension of 55 g of iron powder in 120 ml of 96° ethanol, to which 8.5 ml of water and 6 ml of acetic acid have been added, is heated under reflux. 0.1 mole (26.5 g) of 4-nitro-5-(2',2',2'-trifluoroethyoxy)-1,2-methylenedioxybenzene is added portionwise. Heating is continued for 30 minutes after the end of the addition. The reaction mixture is filtered while boiling. The filtrate, to which 40 ml of a 7N solution of hydrochloric acid in ethanol is added, is evaporated to dryness. The hydrochloride of the expected product is isolated. After being dissolved in water and then neutralized with aqueous ammonia, the expected product precipitates out. After being dried hot under vacuum and then recrystallized from cyclohexane, it melts at 78° C.

Analysis of the product obtained gives the following results:

| Analysis | Calculated for $C_9H_8NO_3F_3$ | Found |
|---|---|---|
| C % | 45.96 | 46.09 |
| H % | 3.43 | 3.43 |
| N % | 5.96 | 5.89 |
| F % | 24.24 | 24.12 |

PREPARATIVE EXAMPLE NO. 4

Preparation of 4-methylamino-5-methoxy-1,2-methylenedioxybenzene

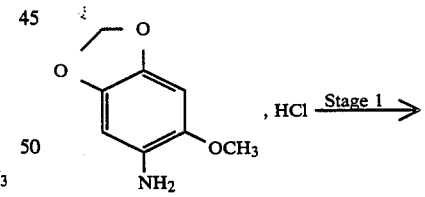

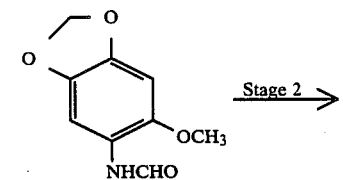

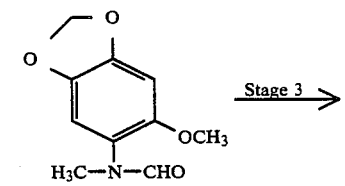

-continued

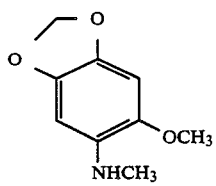

Stage 1: Preparation of 4-N-formylamino-5-methoxy-1,2-methylenedioxybenzene 0.05 mole (9.9 g) of 4-amino-5-methoxy-1,2-methylenedioxybenzene hydrochloride in 40 ml of formamide is heated on a boiling water bath for half an hour. The reaction mixture is cooled. The precipitate of the expected product is filtered off. After being reslurried in water and dried, it melts at 138° C.

Stage 2: Preparation of 4-(N-formyl,N-methyl)-amino-5-methoxy-1,2-methylenedioxybenzene A solution of 0.033 mole (6.5 g) of 4-N-formylamino-5-methoxy-1,2-methylenedioxybenzene in 22 ml of dimethylformamide is prepared. 22.5 ml of a 30% solution of sodium methylate in methanol and 10.5 ml of methyl sulphate are added alternately over 3 hours, the temperature being between 25° C. and 45° C. The reaction mixture is then poured onto 300 g of a mixture of ice and water. The expected product precipitates out. After recrystallization from 96° ethanol it melts at 112° C.

Analysis of the product obtained gives the following results:

| Analysis | Calculated for $C_{10}H_{11}NO_4$ | Found |
|---|---|---|
| C % | 57.41 | 57.34 |
| H % | 5.30 | 5.28 |
| N % | 6.70 | 6.65 |
| O % | 30.59 | 30.83 |

Stage 3: Preparation of 4-methylamino-5-methoxy-1,2-methylenedioxybenzene 0.029 mole (6 g) of the compound prepared during stage 2 is heated for 1 hour under reflux in 50 ml of a 7N alcoholic solution of hydrochloric acid. The reaction mixture is cooled. The hydrochloride of the expected product is filtered off.

After the hydrochloride has been dissolved in the minimum quantity of water and neutralized with aqueous ammonia, the expected product cyrstallizes out. After filtration and drying it melts at 66° C.

Analysis of the product obtained gives the following results:

| Analysis | Calculated for $C_9H_{11}NO_3$ | Found |
|---|---|---|
| C % | 59.66 | 59.52 |
| H % | 6.12 | 6.17 |
| N % | 7.73 | 7.64 |
| O % | 26.49 | 26.54 |

PREPARATIVE EXAMPLE NO. 5

Preparation of 4-amino-5-(β-hydroxyethoxy)-1,2-methylenedioxybenzene hydrochloride

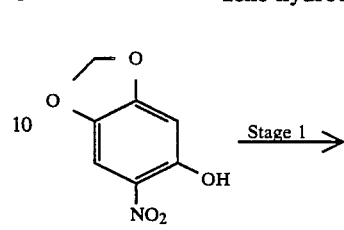

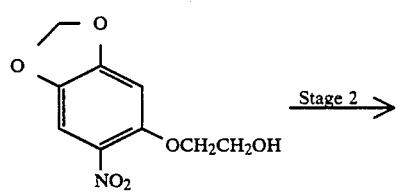

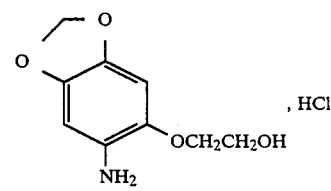

Stage 1: Preparation of 4-nitro-5-(β-hydroxyethyoxy)-1,2-methylenedioxybenzene 0.1 mole (18.3 g) of 4-hydroxy-5-nitro-1,2-methylenedioxybenzene in 60 ml of dimethylformamide, to which 21.3 g of glycol bromhydrin and 22.1 g of potassium carbonate have been added, is heated on a boiling water bath. After 7 hours' heating, the reaction mixture is cooled. The expected product precipitates out. After being recrystallized from 96° ethanol and then from benzene it melts at 122° C.

Analysis of the product obtained gives the following results:

| Analysis | Calculated for $C_9H_9NO_6$ | Found |
|---|---|---|
| C % | 47.58 | 47.70 |
| H % | 3.99 | 4.09 |
| N % | 6.17 | 6.30 |
| O % | 42.26 | 42.35 |

Stage 2: Preparation of 4-amino-5-(β-hydroxyethoxy)-1,2-methylenedioxybenzene hydrochloride A suspension of 23 g of hydrogen-reduced iron powder in 50 ml of 96° ethanol, to which 3.5 ml of water and 2.5 ml of acetic acid have been added, is heated under reflux. 0.042 mole (9.5 g) of 4-nitro-5-(β-hydroxyethoxy)-1,2-methylenedioxybenzene is added portionwise. Heating is continued for 30 minutes after the end of the addition.

After the addition of 40 ml of absolute ethanol, the reaction mixture is filtered while boiling. 17 ml of a 7N solution of hydrochloric acid in ethanol are added to the filtrate to precipitate the hydrochloride of the expected product. The hydrochloride is dissolved in 100 ml of water. After filtration to remove an insoluble brown material and neutralization with aqueous ammonia, 4-amino-5-(β-hydroxyethoxy)-1,2-methylenedioxybenzene precipitates out. After recrystallization from benzene it melts at 102° C.

Elemental analysis of the hydrochloride obtained after purification gives the following results:

| Analysis | Calculated for C9H12NO4Cl | Found |
|---|---|---|
| C % | 46.26 | 46.26 |
| H % | 5.18 | 5.26 |
| N % | 6.00 | 5.90 |
| O % | 27.39 | 27.52 |
| Cl % | 15.17 | 14.94 |

PREPARATIVE EXAMPLE NO. 6

Preparation of 6-amino-5-methoxy-2-methyl-2-propyl-1,3-benzodioxole hydrochloride

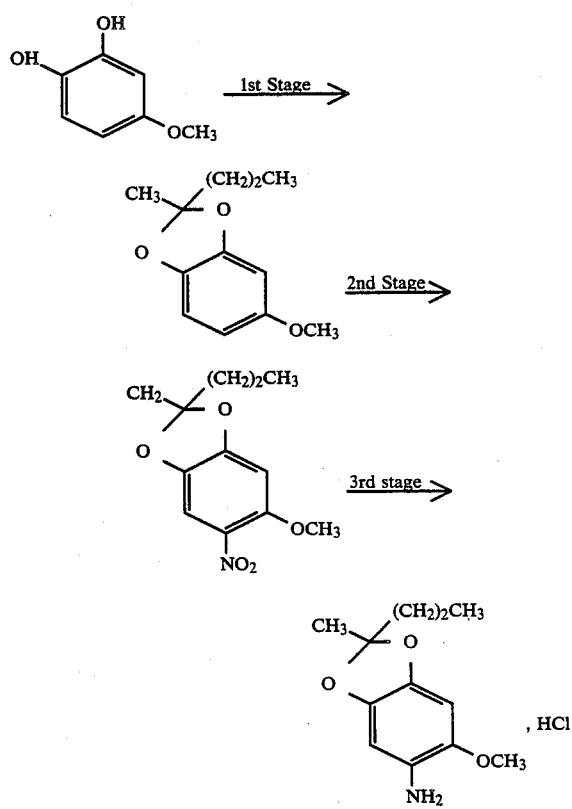

Stage 1:

Preparation of 5-methoxy-2-methyl-2-propyl-1,3-benzodioxole 0.35 mole (48.5 g) of 1,2-dihydroxy-4-methoxybenzene, 0.38 mole (32.7 g) of 2-pentanone and 1 g of p-toluenesulphonic acid are added to 350 ml of benzene. The mixture is heated under benzene reflux in order to remove the water formed. After 50 hours' heating, the reaction mixture is cooled and is then filtered through paper. After evaporation under reduced pressure, a brown oil is obtained and is dissolved in 500 ml of ethyl ether. After extraction with a solution of sodium carbonate in water in order to remove the unreacted 1,2-dihydroxy-4-methoxybenzene, the ethereal phase is dried with sodium sulphate. After evaporation of the ethyl ether under reduced pressure, the expected product is obtained and is employed as such in the following stage.

Stage 2: Preparation of 5-methoxy-6-nitro-2-methyl-2-propyl-1,3-benzodioxole 0.19 mole (40 g) of 5-methoxy-2-methyl-2-propyl-1,3-benzodioxole prepared in the preceding stage is dissolved in 100 ml of acetic acid. After the solution prepared in this manner has been cooled to 15° C., a solution consisting of 14.7 ml of nitric acid (d=1.40) and 15 ml of acetic acid is added dropwise over a quarter of an hour. Cooling is applied to keep the temperature between 20° C. and 24° C. Stirring is continued for 15 minutes after the end of the addition.

The reaction mixture is poured onto 350 g of iced water. The expected product precipitates out. The precipitate is filtered off and is washed with water and with isopropanol. After drying, it is recrystallized from 50 ml of 96° ethyl alcohol. It melts at 67° C.

Analysis of the product obtained gives the following results:

| Analysis | Calculated for C12H15NO5 | Found |
|---|---|---|
| C % | 56.91 | 56.74 |
| H % | 5.97 | 6.00 |
| N % | 5.53 | 5.62 |
| O % | 31.59 | 31.85 |

Stage 3:

Reduction of 5-methoxy-6-nitro-2-methyl-2-propyl-1,3-benzodioxole

A suspension of 50 g of hydrogen-reduced iron powder in 150 ml of ethanol, to which 7 ml of water and 5 ml of acetic acid have been added, is heated under reflux. 0.08 mole (20.3 g) of 5-methoxy-6-nitro-2-methyl-2-propyl-1,3-benzodioxole is added portionwise. Heating is continued for 30 minutes after the end of the addition. The reaction mixture is filtered while boiling. 25 ml of a 7N solution of hydrochloric acid is added to the filtrate.

After evaporation, a dry extract of the expected product is obtained. The dry extract is washed with absolute ethanol.

After drying, analysis of the product obtained gives the following results:

| Analysis | Calculated for C12H17NO3Cl | Found |
|---|---|---|
| C % | 55.49 | 55.61 |
| H % | 6.99 | 7.00 |
| N % | 5.39 | 5.37 |
| O % | 18.48 | 18.55 |
| Cl % | 13.65 | 13.60 |

APPLICATION EXAMPLE NO. 1

The following dyeing mixture is prepared:

| | |
|---|---|
| 4-Amino-5-methoxy-1,2-methylenedioxybenzene hydrochloride | 0.509 g |
| 4-Amino-N—β-methoxyethylaniline dihydrochloride | 0.597 g |
| Alfol C 16/18 - Condea company (50/50 cetylstearyl alcohol) | 8.00 g |
| Lanette Wax E - Henkel company (sodium cetylstearyl sulphate) | 0.50 g |
| Cemulsol B - Rhone-Poulenc (ethoxylated castor oil) | 1.00 g |
| Oleoyl diethanolamide | 1.50 g |

-continued

| | |
|---|---|
| Masquol DTPA - Protex company (pentasodium salt of diethylene triamine pentaacetic acid) | 2.50 g |
| 20% aqueous ammonia | 11.00 g |
| Water q.s. | 100 g |
| pH = 9.9 | |

100 g of 20-volume hydrogen peroxide are added at the time of use. When applied to 90% naturally white hair for 20 minutes at 30° C., the mixture imparts to it, after shampooing and rinsing, a light olive-green colour.

APPLICATION EXAMPLE NO. 2

The following dyeing mixture is prepared:

| | |
|---|---|
| N,N—di(β-hydroxyethyl)-para-phenylenediamine dihydrochloride | 0.67 g |
| 4-(β-hydroxyethyl)amino-5-methoxy-1,2-methylenedioxybenzene | 0.53 g |
| Alfol C 16/18 - Condea company (50/50 cetylstearyl alcohol) | 19.00 g |
| Eutanol G - Henkel company (2-octyldodecanol) | 4.5 g |
| Mergital C.S. - Henkel company (cetyl stearyl alcohol containing 15 moles of ethylene oxide) | 2.5 g |
| Ammonium lauryl sulphate | 10.0 g |
| Polymer B | 4.0 g |
| Cationic polymer consisting of the following repeat units: | |

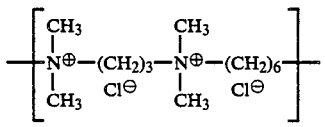

| | |
|---|---|
| Benzyl alcohol | 2.0 g |
| 20% aqueous ammonia | 11.0 g |
| Trilon B (ethylenediaminetetraacetic acid) | 1.0 g |
| 35° Be sodium bisulphite | 1.2 g |
| Water q.s. | 100 g |
| pH = 9.7 | |

90 g of 20-volume hydrogen peroxide are added at the time of use. When applied to bleached hair for 20 minutes at 30° C., the mixture imparts to it, after shampooing and rinsing, a medium olive-green colour.

APPLICATION EXAMPLE NO. 3

The following dyeing mixture is prepared:

| | |
|---|---|
| 4-Amino-5-(β-hydroxyethoxy)-1,2-methylenedioxybenzene hydrochloride | 0.584 g |
| p-Phenylenediamine | 0.27 g |
| Oleyl alcohol polyglycerolated with 2 moles of glycerol | 4.50 g |
| Oleyl alcohol polyglycerolated with 4 moles of glycerol | 4.50 g |
| Ethomeen 0 12 -Armoon Hess Chemical company Ltd (oleylamine oxyethylenated with 12 moles of ethylene oxide) | 4.50 g |
| Comperlan KD - Henkel company (copra diethanolamide) | 9.00 g |
| Propylene glycol | 4.00 g |
| 2-Butoxyethanol | 8.00 g |
| 96° ethanol | 6.00 g |
| Masquol DTPA - Protex company (pentasodium salt of diethylenetriaminepentaacetic acid) | 2.00 g |
| Hydroquinone | 0.15 g |
| 35° Be sodium bisulphite solution | 1.30 g |

-continued

| | |
|---|---|
| 20% aqueous ammonia | 10.00 g |
| Water q.s. | 100 g |
| pH = 10.1 | |

100 g of 20-volume hydrogen peroxide are added at the time of use. When applied to bleached hair for 20 minutes at 30° C., the mixture imparts to it, after shampooing and rinsing, a lime-green colour.

APPLICATION EXAMPLE NO. 4

The following dyeing mixture is prepared:

| | |
|---|---|
| 4-(β-hydroxyethyl)amino-5-methoxy-1,2-methylenedioxybenzene | 0.53 g |
| 4-Amino-N—β-methoxyethylaniline dihydrochloride | 0.509 g |
| Carbopol 934 - Goodrich Chemicals company | 3.00 g |
| 96° alcohol | 11.00 g |
| 2-Butoxyethanol | 5.00 g |
| Trimethylcetylammonium bromide | 2.00 g |
| Trilon B (ethylenediaminetetraacetic acid) | 0.20 g |
| 20% aqueous ammonia | 10.00 g |
| 35° Be sodium bisulphite | 1.00 g |
| Water q.s. | 100 g |
| pH = 9.6 | |

100 g of 20-volume hydrogen peroxide are added at the time of use. When applied to bleached hair for 20 minutes at 30° C., the mixture imparts to it, after shampooing and rinsing, a pale olive-green colour.

APPLICATION EXAMPLE NO. 5

The following dyeing mixture is prepared:

| | |
|---|---|
| 6-Amino-5-methoxy-2-methyl-2-propyl-1,3-benzodioxole hydrochloride | 1.30 g |
| 2,5-Diaminotoluene dihydrochloride | 0.97 g |
| Cemulsol NP4 - Rhone-Poulenc (nonylphenol containing 4 moles of ethylene oxide) | 21.00 g |
| Cemulsol NP9 - Rhone-Poulenc (nonylphenol containing 9 moles of ethylene oxide) | 24.00 g |
| Oleic acid | 4.00 g |
| 2-Butoxyethanol | 3.00 g |
| 96° ethanol | 10.00 g |
| Masquol DTPA - Protex company (pentasodium salt of diethylenetriaminepentaacetic acid) | 2.50 g |
| 35° Be sodium bisulphite solution | 1.00 g |
| 20% aqueous ammonia | 10.00 g |
| Water q.s. | 100 g |
| pH = 10 | |

100 g of 20-volume hydrogen peroxide are added at the time of use. When applied to permanent-waved hair for 35 minutes at 30° C., the mixture imparting to it, after shampooing and rinsing, a golden light-bronze colour.

APPLICATION EXAMPLE NO. 6

The following dyeing mixture is prepared:

| | |
|---|---|
| 4-Amino-3-methoxyphenol | 1.00 g |
| 4-Amino-5-methoxy-1,2-methylenedioxybenzene hydrochloride | 1.30 g |
| Carboxymethyl cellulose | 2.00 g |
| Ammonium lauryl sulphate | 5.00 g |
| Propylene glycol | 8.00 g |
| 2-Butoxyethanol | 8.00 g |

| | |
|---|---|
| Masquol DTPA - Protex company (pentasodium salt of diethylenetriaminepentaacetic acid) | 2.00 g |
| Ammonium acetate | 1.00 g |
| Thioglycolic acid | 0.40 g |
| 20% aqueous ammonia | 10.00 g |
| Water q.s. | 100 g |
| pH = 11.5 | |

100 g of 20-volume hydrogen peroxide are added at the time of use. When applied to 90% naturally white hair for 30 minutes at 28° C., the mixture imparts to it, after shampooing and rinsing, a green blond colour.

We claim:

1. Dyeing composition for keratinous fibres and especially for human hair, comprising in a cosmetically acceptable solvent medium, a tinctorially effective amount of at least one para-type oxidation dye precursor in combination with at least one heterocyclic coupler of formula:

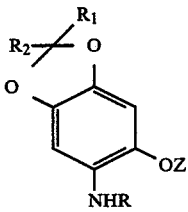

in which R denotes a hydrogen atom, a $C_1$–$C_4$ alkyl radical, a $C_2$–$C_4$ hydroxyalkyl radical, a $C_3$ to $C_6$ polyhydroxyalkyl radical or a $C_2$–$C_6$ alkyl radical; independently of R, Z denotes a $C_1$–$C_4$ alkyl radical, a $C_2$–$C_4$ hydroxyalkyl radical, a $C_3$–$C_6$ polyhydroxyalkyl radical, a $C_2$–$C_6$ alkoxy-alkyl radical or a trifluoroethyl radical, and $R_1$ and $R_2$ independently of each other denote a hydrogen atom or a $C_1$–$C_4$ alkyl radical, or an addition salt of the compound of formula (I) with an inorganic acid.

2. Dyeing composition according to claim 1, wherein in the heterocyclic coupler of formula (I), R and Z do not simultaneously denote a polyhydroxyalkyl radical.

3. Dyeing composition according to claim 1, wherein R denotes a hydrogen atom or a methyl, ethyl, n-propyl, n-butyl, β-hydroxyethyl, β-hydroxypropyl, γ-hydroxypropyl or β,γ-dihydroxypropyl radical and Z denotes a methyl, ethyl, n-propyl, n-butyl, β-hydroxyethyl, β-hydroxypropyl, β-hydroxypropyl, β,γ-dihydroxypropyl or trifluoroethyl radical.

4. Dyeing composition according to claim 1 which contains at least one heterocyclic coupler of formula (I) selected from the group consisting of methoxy-1,2-methylenedioxybenzene, 4-(β-hydroxyethyl)amino-5-methoxy-1,2-methylenedioxybenzene, 4-amino-5-(2′,2′,2′-trifluoroethoxy)-1,2-methylenedioxybenzene, 4-methylamino-5-methoxy-1,2-methylenedioxybenzene, 4-amino-5-(β-hydroxyethoxy)-1,2-methylenedioxybenzene, 6-amino-5-methoxy-2-methyl-2-propyl-1,3-benzodioxole and their addition salts with an inorganic acid.

5. Dyeing composition according to claim 1 containing from 0.05 to 3.5% by weight of one or more heterocyclic couplers of formula (I) or of their addition salts with an inorganic acid.

6. Dyeing composition according to claim 1 wherein the para-oxidation dye precursor is selected from the group consisting of p-phenylenediamines, p-aminophenols, para-heterocyclic compounds and mixtures thereof.

7. Dyeing composition according to claim 6, wherein the p-phenylenediamines correspond to the formula:

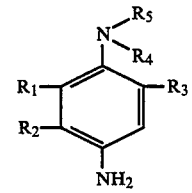

in which $R_1$, $R_2$ and $R_3$ are identical or different and denote a hydrogen or halogen atom, a $C_1$–$C_4$ alkyl radical, a $C_1$–$C_4$ alkoxy radical, $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ containing from 1 to 4 carbon atoms, or else $R_4$ and $R_5$, together with the nitrogen atom to which they are linked, can form a piperidino or morpholino heterocyclic ring provided that $R_1$ or $R_3$ or both $R_1$ and $R_3$ denote a hydrogen atom when $R_4$ and $R_5$ do not denote a hydrogen atom, or can be a cosmetically acceptable salt of the compound of formula (XII).

8. Dyeing composition according to claim 7, wherein the p-phenylenediamine is selected from the group consisting of p-phenylenediamine, p-tolylenediamine, methoxyparaphenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di(β-hydroxyethyl)-para-phenylenediamine, 3-methyl-4-amino-N,N-di(β-hydroxyethyl)aniline, 3-chloro-4-amino-N,N-di(β-hydrooxyethyl)aniline, 4-amino-N,N-(ethyl, carbamylmethyl)aniline, 3-methyl-4-amino-N,N-(ethyl, carbamylmethyl)aniline, 4-amino-N,N-(ethyl, β-piperidinoethyl)aniline, 3-methyl-4-amino-N,N-(ethyl, β-piperidinoethyl)aniline, 4-amino-N,N-(ethyl, β-morpholinoethyl)aniline, 3-methyl-4-amino-N,N-(ethyl, β-morpholinoethyl)aniline, 4-amino-N,N-(ethyl, β-acetylaminoethyl)aniline, 4-amino-N,β-methoxethylaniline, 3-methyl-4-amino-N,N-(ethyl, β-acetyl-aminoethyl)aniline, 4-amino-N,N-(ethyl, β-mesylaminoethyl)-aniline, 3-methyl-4-amino-N,N-(ethyl, β-mesylaminoethyl)-aniline, 4-amino-N,N-(ethyl, β-sulphoethyl)aniline, 3-methyl-4-amino-N,N-(ethyl, β-sulphoethyl)aniline, N-[(4′-amino)phenyl]morpholine and N-[(4′-amino)phenyl]piperidine, in the form of free base or in the form of a cosmetically acceptable salt.

9. Dyeing composition according to claim 6, comprising at least one p-aminophenol selected from the group consisting of p-aminophenols, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

10. Dyeing composition according to claim 1 comprising a total amount from 0.3 to 7% by weight of one or more para-type oxidation dye precursors and of one or more heterocyclic couplers of formula (I) or of their salts.

11. Dyeing composition according to claim 1 additionally comprising ortho-type dye precursors selected from the group consisting of ortho-aminophenols, ortho-phenylenediamines and ortho-diphenols.

12. Dyeing composition according to claim 1, also comprising other couplers selected from the group consisting of meta-diphenols, meta-aminophenols, meta-phenylenediamines, meta-acylaminophenols, meta-ureidophenols, meta-carbalkoxyaminophenols, α-naphthol, β-ketonic compounds and pyrazolones.

13. Dyeing composition according to claim 1, also comprising direct dyes selected from the group consisting of azo and anthraquinone dyes and the nitro derivatives of the benzene series.

14. Dyeing composition according to claim 1 having a pH between 8 and 11 and preferably between 9 and 11.

15. Dyeing composition according to claim 1, containing from 1 to 40% by weight of an organic solvent selected from the group consisting of $C_1$–$C_4$ alkanols, glycerol, glycols or glycol ethers, aromatic alcohols and mixtures thereof.

16. Dyeing composition according to claim 1, also containing from 0.5 to 55% by weight of at least one anionic, cationic, nonionic or amphoteric surface-active agent or mixtures thereof.

17. Dyeing composition according to claim 1, also comprising cosmetic adjuvants selected from the group consisting of thickeners, antioxidants, penetrating agents, sequestering agents, buffers, perfumes and alkalifying or acidifying agents.

18. Process for dyeing keratinous fibres and especially human hair according to a process making use of development with an oxidizing agent, which consists in mixing the dyeing composition according to claim 1 with an oxidizing solution, in a sufficient quantity, at the same time of use and then applying the mixture obtained to the hair, leaving it in position for 10 to 40 minutes, preferably 15 to 30 minutes, and then rinsing the hair, washing it with a shampoo, rinsing it again and drying it.

19. Process for dyeing keratinous fibres and especially human hair according to a process making use of development with an oxidizing agent, which consists in first applying to the keratinous fibres a dyeing composition containing at least one para-type oxidation dye precursor such as defined in claim 6, then applying a dyeing composition containing at least one coupler of formula (I) according to claim 1, the oxidizing agent being present in the composition which is applied in the second step or else added onto the keratinous fibres themselves in a third step, leaving in position for 10 to 40 minutes, preferably 15 to 30 minutes, and then rinsing the hair, washing it with a shampoo, rinsing it again and drying it.

20. Heterocyclic coupler of formula:

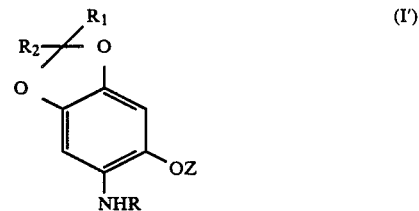

in which R denotes a hydrogen atom, a $C_1$–$C_4$ alkyl radical, a $C_2$ to $C_4$ hydroxyalkyl radical, a $C_3$ to $C_6$ polyhydroxyalkyl radical or a $C_2$–$C_6$ alkoxyalkyl radical and Z denotes a $C_1$ to $C_4$ alkyl, $C_2$ to $C_4$ hydroxyalkyl, $C_3$ to $C_6$ polyhydroxyalkyl or $C_2$–$C_6$ alkoxyalkyl radical or a trifluoroethyl radical, $R_1$ and $R_2$ independently of each other denote a hydrogen atom of a $C_1$14 $C_4$ alkyl radical, provided that when R, $R_1$ and $R_2$ denotes a hydrogen atom, Z does not denote a methyl radical.

21. Heterocyclic coupler according to claim 20, consisting in a compound of formula (I') in which R and Z do not simultaneously denote a polyhydroxyalkyl radical.

22. Heterocyclic coupler according to claim 20 wherein R denotes a hydrogen atom or a methyl, ethyl, n-propyl, n-butyl, β-hydroxyethyl, γ-hydroxypropyl, γ-hydroxypropyl or β,γ-dihydroxypropyl radical and Z denotes a methyl, ethyl, n-propyl, n-butyl, β-hydroxyethyl, β-hydroxypropyl, γ-hydroxypropyl, β,65-dihydroxypropyl or trifluoroethyl radical.

23. Heterocyclic coupler according to claim 20 selected from the group consisting of 4-(β-hydroxyethyl)amino-5-methoxy-1,2-methylenedioxybenzene, 4-amino-5-(2',2',2'-trifluoroethoxy)-1,2-methylenedioxybenzene, 4-methylamino-5-methoxy-1,2-methylenedioxybenzene, 4-amino-5-(β-hydroxyethoxy)-1,2-methylenedioxybenzene, 6-amino-5-methoxy-2-methyl-2-propyl-1,3-benzodioxole and their addition salts with an inorganic acid.

* * * * *